United States Patent [19]
McGonigle et al.

[11] Patent Number: 5,962,229
[45] Date of Patent: Oct. 5, 1999

[54] MAIZE GLUTATHIONE-S-TRANSFERASE ENZYMES

[75] Inventors: Brian McGonigle, Wilmington, Del.; Daniel P. O'Keefe, Ridley Park, Pa.

[73] Assignee: E.I. du Pont de Nemours and Company, Wilmington, Del.

[21] Appl. No.: 08/924,759

[22] Filed: Sep. 5, 1997

[51] Int. Cl.$^6$ .............................. C07H 21/04; C12Q 1/68; C12N 9/10
[52] U.S. Cl. ........................ 435/6; 435/193; 435/252.33; 435/410; 435/320.1; 536/23.1; 536/23.2; 536/23.6
[58] Field of Search ................... 435/193, 252.3, 435/252.33, 410, 320.1, 6; 536/23.2, 23.6, 23.1

[56] References Cited

U.S. PATENT DOCUMENTS 5,073,677  12/1991  Helmer et al. ........................... 800/205
5,589,614  12/1996  Bridges et al. .......................... 800/205

FOREIGN PATENT DOCUMENTS

WO 97/11189  3/1997  WIPO .

OTHER PUBLICATIONS

Dixon et al. Genebank; Sequence ID: ZMY12862; AC: Y12862; NI: e1049060, Jul. 30, 1997.

Itzhaki et al. "Characterization of an ethylene–responsive glutathione S–transferase gene cluster in Carnation" Plant Mol. Biol. 22, 43–58, 1993.

Irzyk et al. in "regulation of enzymatic systems detoxifying xenobiotics in plants" Hatzios, K. K., Editor, Kluwer Academic Press, Boston, pp. 155–170, 1997.

Frova et al. in "regulation of enzymatic systems detoxifying xenobiotics in plants" Hatzios, K. K., Editor, Boston, pp. 171–181, 1997.

David C. Holt et al., Characterization of the Safener–Induced Glutathione S–Transferase Isoform II from Maize, *Planta*, 196, 295–302, 1995.

F. Droog, Plant Glutathione S–Transferases, a Tale of Theta and Tau, *J. Plant Growth Regul*, 16, 95–107, 1997.

Laura Rossini et al., Characterization of Glutathione S–Transferase Isoforms in Three Maise Inbred Lines Exhibiting Differential Sensitivity to Alachlor, *Plant Physiol*, 112, 1595–1600, 1996.

Kathleen A. Marrs, The Functions and Regulation of Glutathione S–Transferases in Plants, *Annu. Rev. Plant Physiol. Plant Mol. Biol.*, 47, 127–158, 1996.

Sharad S. Singhal et al., Purification and Characterization of Glutathione S–Transferase from Sugarcane Leaves, *Phytochemistry*, 30, No. 5, 1409–1414, 1991.

Robert Edwards et al., Glutathione Transferases in Wheat (Triticum) Species with Activity toward Fenoxaprop–Ethyl and Other Herbicides, *Pesticide Biochemistry and Physiology*, 54, 94–104, 1996.

Michael A. Wosnick et al., Total Chemical Synthesis and Expression in *Escherichia coli* of a Maize GlutathioneTransferase (GST) Gene, *Gene*, 76, 153–160, 1989.

Ian Jepson et al., Cloning and Characterization of Maize Herbicide Safener–induced cDNAs Encoding Subunits of Glutathione S–Transferase Isoforms, I, II, and IV, *Plant Molecular Biology*, 26, 1855–1866, 1994.

Dianne A.M. van der Kop et al., Isolation and Characterization of an Auxin–Inducible Glutathione S–Transferase Gene of Arabidopsis Thaliana, *Plant Molecular Biology*, 30, 839–844, 1996.

Dilip M. Shah et al., Structural Analysis of a Maize Gene Coding for Glutathione–S–Transferase Involved in Herbicide Detoxification, *Plant Molecular Biology*, 6, 203–211, 1986.

Robert E. Moore et al., Cloning and Expression of a cDNA Encoding a Maize Glutathione–S–Transferase in *E. Coli*, *Nucleic Acids Research*, 14, No. 18, 7227–7235, 1986.

Kriton K. Hatzios et al., Herbicide Safeners, *J. Environ. Sci. Health*, B31(3), 545–553, 1996.

Thomas Flury et al., A 2,4–D–Inducible Glutathione S–Transferase from Soybean (Glycine Max)., *Physiologia Plantarum*, 94, 312–318, 1995.

Robert Edwards, Characterization of Glutathione Transferases and Glutathione Peroxidases in Pea, *Physiologia Plantarum*, 98, 594–604, 1996.

*Primary Examiner*—Robert A. Wax
*Assistant Examiner*—Nashaat T. Nashed

[57] ABSTRACT

This invention relates to isolated nucleic acid fragments encoding all or a substantial portion of maize glutathione-S-transferase (GST) enzymes involved in the detoxification of xenobiotic compounds in plants and seeds. The invention also relates to the construction of chimeric genes encoding all or a substantial portion of maize GST enzymes, host cells transformed with those genes and methods of the recombinant production of maize GST enzymes. Methods of constructing transgenic plants having altered levels of GST enzymes and screens for identifying maize GST enzyme substrates and maize GST enzyme inhibitor, are also provided.

9 Claims, No Drawings

5,962,229

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 844 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (F) TISSUE TYPE: MAIZE (vii) IMMEDIATE SOURCE:
      (B) CLONE: BMS1.PK0023.G8

(xi) SEQUENCE DESCRIPTION: SEQ ID NO:1:

```
CGGCACGAGC AATGGCGCCG CCGATGAAGG TGTACGGGTG GGCCGTGTCG CCGTGGATGG      60

CGCGCGCGCT GGTGTGTCTG GAGGAGGCCG GCGCCGACTA CGAGATCGTC CCCATGAGCA     120

GGTGTGGCGG CGACCACCGC CGGCCGGAGC ACCTCGCCAA AAACCCGTTC GGTGAAATCC     180

CAGTTTTAGA GGACGGTGAT CTCACGCTCT ACCAATCACG CGCCATCGCA CGGTACGTCC     240

TCCGCAAGCT CAAGCCAGAG CTCCTCCGCG AAGGCGACCT CGAGGGGTCG GCGATGGTGG     300

ACGCGTGGAT GGAGGTGGAA GCCCACCACA TGGAGCCGGC CCTGTGGCCC ATCATCCGCC     360
```

-continued

```
ACAGCATCAT CGGCCAGTAC GTCGGCCGCG AGCGCGACCA CCAGGCCGTC ATCGACGAGA      420

ACCTCGACAG GCTGAGGAAG GTGCTGCCGG CGTACGAGGC GAGGCTGTCC GTCTGCAAGT      480

ACCTGGTGGG GGACGACATC AGCGCCGCCG ACCTCTGCCA CTTCGGCTTC ATGCGCTACT      540

TCATGGCCAC GGAGTACGCC GGCTTGGTGG ACGCGTACCC GCACGTCAAG GCCTGGTGGG      600

ACGCGCTGCT GGCGAGGCCC TCGGTGCAGA AGGTCATGGC AGGCATGCCG CCGGATTTTG      660

GGTACGCCAG CGGGAACATA CCATAGGCTA GAAGCGGTGG GCGTCCGTCA TTCTGCAGAT      720

CTGAGGTCTC TGAACCTCAG CGTTTCCGAT AAACATGCAT GCTTTATGTA CTGTTTAAAA      780

AACAAACCTG ATTGGTGCAG GGTATTTTAG TCCTCTTAAA AAAAAAAAAA AAAAAAAAA      840

AAAA                                                                    844
```

(2) INFORMATION FOR SEQ ID NO:2:

(i) SEQUENCE CHARACTERISTICS:
        (A) LENGTH: 224 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (B) CLONE: BMS1.PK0023.G8

(xi) SEQUENCE DESCRIPTION: SEQ ID NO:2:

```
Met Ala Pro Pro Met Lys Val Tyr Gly Trp Ala Val Ser Pro Trp Met
1               5                   10                  15

Ala Arg Ala Leu Val Cys Leu Glu Glu Ala Gly Ala Asp Tyr Glu Ile
                20                  25                  30

Val Pro Met Ser Arg Cys Gly Gly Asp His Arg Arg Pro Glu His Leu
            35                  40                  45

Ala Lys Asn Pro Phe Gly Glu Ile Pro Val Leu Glu Asp Gly Asp Leu
        50                  55                  60

Thr Leu Tyr Gln Ser Arg Ala Ile Ala Arg Tyr Val Leu Arg Lys Leu
65                  70                  75                  80

Lys Pro Glu Leu Leu Arg Glu Gly Asp Leu Glu Gly Ser Ala Met Val
                85                  90                  95

Asp Ala Trp Met Glu Val Glu Ala His His Met Glu Pro Ala Leu Trp
            100                 105                 110

Pro Ile Ile Arg His Ser Ile Ile Gly Gln Tyr Val Gly Arg Glu Arg
        115                 120                 125

Asp His Gln Ala Val Ile Asp Glu Asn Leu Asp Arg Leu Arg Lys Val
    130                 135                 140

Leu Pro Ala Tyr Glu Ala Arg Leu Ser Val Cys Lys Tyr Leu Val Gly
145                 150                 155                 160

Asp Asp Ile Ser Ala Ala Asp Leu Cys His Phe Gly Phe Met Arg Tyr
                165                 170                 175

Phe Met Ala Thr Glu Tyr Ala Gly Leu Val Asp Ala Tyr Pro His Val
            180                 185                 190

Lys Ala Trp Trp Asp Ala Leu Leu Ala Arg Pro Ser Val Gln Lys Val
        195                 200                 205

Met Ala Gly Met Pro Pro Asp Phe Gly Tyr Ala Ser Gly Asn Ile Pro
    210                 215                 220
```

(2) INFORMATION FOR SEQ ID NO:3:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: MAIZE (vii) IMMEDIATE SOURCE:
        (B) CLONE: CS.PK0010.C5

(xi) SEQUENCE DESCRIPTION: SEQ ID NO:3:

```
ATCACCATTC TTCATCCCTC GTTGTCATCT CACAGCTTGG GCTAGAGACC AAACAAACCA      60

AAGGGAAGCA TGGCAGCAGG CCTGCAAGTG TTTGGCCAGC CGGCGTCTAC TGATGTTGCC     120

AGGGTTCTGA CGTGCCTGTT TGAGAAGAAA TTGGAGTTTG AGCTTGTCCG CATTGATACA     180

TTTAAGACAC ATCACAGGCT TCCTGAGTTC ATCAGGCTGC GGGATCCGAA TGGGCAAGTG     240

ACCTTCAAGC ATGGCGACAA AACCCTTGTT GATTCAAGGG ACATATGCCG GTACGTTTGC     300

AACCAGTTTC CAAATTACGG AAACAAGAGC CTCTATGGAT CTGGTGCTCT AGAACGGGCA     360

TCGATAGAAC AGTGGCTCCA GGCAGAAGCC CAGAACTTTG CCCTCCCAG CTCTGCGCTT      420

GTGTTTCAGC TGGCGTTCGT TCCGCACCTC AGTCACCTGG GCGTTCGTCA GGACCCTGCT     480

GTTATTGCTG AAAACGAGGA CAAACTGAAG CAGGTTCTTG ATGTTTACGA CGAAATACTC     540

TCCAAGAACG AGTACCTGGC TGGTGATGAG TTCACCCTGG CCGACCTGTC TCACCTTCCG     600

AACTCGCACT ACATCGTAAA CACCGAGAGA GGAAGGAAGC TCTTCACCAA CAAGAAGAAT     660

GTGGCGAAAT GGTATGACAG GCTCTCGAAG CGCGAGACAT GGGTGCAGGT CGTCAAGATG     720

CAGAAGGAAC ATCCTGGTGC GTTCAAGTAA TGGCTTGTCT TGGGGAGTTG TGAGTATGGC     780

TTCATCGTCC GTGTTGGTCT GGCTCATCAG TGTTAAAAGC CCATCAGTGT CGTCAACCAG     840

AATAATGTGA AGCCCAACTG TGATGTATGG TCTTTTTTTT TTAAAAGCGC ATTTGTAAAC     900

TATTGGCTAT TTCTTGCACG TGCCAATTCA TCGTCACATA TAAAATAAAC TGTATCTTTG     960

ACCTTGTGTC ATGTACGCAA AAAAAAAAAA AAAAAAAA                             999
```

(2) INFORMATION FOR SEQ ID NO:4:

(i) SEQUENCE CHARACTERISTICS:
        (A) LENGTH: 226 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (A) LIBRARY: CS.PK0010.C5

(xi) SEQUENCE DESCRIPTION: SEQ ID NO:4:

```
Met Ala Ala Gly Leu Gln Val Phe Gly Gln Pro Ala Ser Thr Asp Val
1               5                   10                  15

Ala Arg Val Leu Thr Cys Leu Phe Glu Lys Lys Leu Glu Phe Glu Leu
            20                  25                  30
```

```
Val Arg Ile Asp Thr Phe Lys Thr His His Arg Leu Pro Glu Phe Ile
         35                  40                  45
Arg Leu Arg Asp Pro Asn Gly Gln Val Thr Phe Lys His Gly Asp Lys
     50                  55                  60
Thr Leu Val Asp Ser Arg Asp Ile Cys Arg Tyr Val Cys Asn Gln Phe
 65                  70                  75                  80
Pro Asn Tyr Gly Asn Lys Ser Leu Tyr Gly Ser Gly Ala Leu Glu Arg
                 85                  90                  95
Ala Ser Ile Glu Gln Trp Leu Gln Ala Glu Ala Gln Asn Phe Gly Pro
            100                 105                 110
Pro Ser Ser Ala Leu Val Phe Gln Leu Ala Phe Val Pro His Leu Ser
        115                 120                 125
His Leu Gly Val Arg Gln Asp Pro Ala Val Ile Ala Glu Asn Glu Asp
    130                 135                 140
Lys Leu Lys Gln Val Leu Asp Val Tyr Asp Glu Ile Leu Ser Lys Asn
145                 150                 155                 160
Glu Tyr Leu Ala Gly Asp Glu Phe Thr Leu Ala Asp Leu Ser His Leu
                165                 170                 175
Pro Asn Ser His Tyr Ile Val Asn Thr Glu Arg Gly Arg Lys Leu Phe
            180                 185                 190
Thr Asn Lys Lys Asn Val Ala Lys Trp Tyr Asp Arg Leu Ser Lys Arg
        195                 200                 205
Glu Thr Trp Val Gln Val Val Lys Met Gln Lys Glu His Pro Gly Ala
    210                 215                 220
Phe Lys
225

(2) INFORMATION FOR SEQ ID NO:5:

(i) SEQUENCE CHARACTERISTICS:
        (A) LENGTH:  900 base pairs
        (B) TYPE:  nucleic acid
        (C) STRANDEDNESS:  single
        (D) TOPOLOGY:  linear (ii) MOLECULE TYPE:  cDNA (iii) HYPOTHETICAL:  NO (iv) ANTI-SENSE:  NO (vi) ORIGINAL SOURCE:
         (F) TISSUE TYPE:  MAIZE (vii) IMMEDIATE SOURCE:
         (B) CLONE:  CEB1.PK0017.A5

(xi) SEQUENCE DESCRIPTION:  SEQ ID NO:5:

CCCCAGCGGC GGCGAGGCGA TGGCGGCGCC TGTGACGGTG TACGGACCGA TGCTCTCACC      60

AGCTGTGGCC CGCGTGGCGG CCTGCCTCCT GGAGAAGGAC GTGCCGTTCC AGATCGAGCC     120

GGTGGACATG TCCAAGGGCG AGCACAAGTC GCCGTCCTTC CTCAAGCTCC AGCCCTTCGG     180

ACAGGTCCCT GCCTTCAAGG ACCACCTCAC AACCGTCTTT GAGTCAAGGG CTATTTGCCG     240

TTACATATGC GACCAGTATG CGGACTCTGG TAATCAGGCC CTCTTCGGCA AGAAAGAAGA     300

CGGCGCGGTT GGCCGCGCTG CCATTGAACA GTGGATAGAG TCTGAAGGCC AGAGCTTTAA     360

CCCACCGAGC TTGGCTATTA TCTTCCAGCT CGCATTTGCA CCGATGATGG GCCGGACCAC     420

TGACCTGGCT GTGGTTGAGC AAATGAAGCG AAGCTTGCGA AGGTGCTTGA TGTGTATGAC     480

CAACGGCTGG GGGAGAGCCA GTATTTTGCT GGTGATGATT CTCCCCCTGG CCGACCTTGT     540
```

```
GCACTTGCCC AATGCAGATT TCCTTGTGAA CAGAACCAGC AAGGCTGGCT TGATCACCGA    600

GAGAAAGAAT CTTGCTAGAT GGTGGGATGA TGTCTCGTCC CGACCTGCAT GGAAAAAGGT    660

CACTGAGATG CAGAGCACGC CGAGGCCCTC TTAGAGCTTT TTTTTGGGTT TCTTTGAGCA    720

GCTTCTGATG GCAATTAGTT GCATTCTCCT TGTTTTGTCA TCAAGTCCTT GTCTGTACCG    780

TTTCCTGTTC TCTTATTTAT CGGTCTTAAT TCTTGATCTA TGTATGGTTT GGATCTGTTC    840

TTCTGGTCCT TTAGTTTATA TAAGTACCTA CAATTCTTCA AAAAAAAAAA AAAAAAAAA     900
```

(2) INFORMATION FOR SEQ ID NO:6:

(i) SEQUENCE CHARACTERISTICS:
        (A) LENGTH: 199 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (B) CLONE: CEB1.PK0017.A5

(xi) SEQUENCE DESCRIPTION: SEQ ID NO:6:

```
Met Ala Ala Pro Val Thr Val Tyr Gly Pro Met Leu Ser Pro Ala Val
1               5                  10                  15

Ala Arg Val Ala Ala Cys Leu Leu Glu Lys Asp Val Pro Phe Gln Ile
            20                  25                  30

Glu Pro Val Asp Met Ser Lys Gly Glu His Lys Ser Pro Ser Phe Leu
        35                  40                  45

Lys Leu Gln Pro Phe Gly Gln Val Pro Ala Phe Lys Asp His Leu Thr
    50                  55                  60

Thr Val Phe Glu Ser Arg Ala Ile Cys Arg Tyr Ile Cys Asp Gln Tyr
65                  70                  75                  80

Ala Asp Ser Gly Asn Gln Ala Leu Phe Gly Lys Lys Glu Asp Gly Ala
                85                  90                  95

Val Gly Arg Ala Ala Ile Glu Gln Trp Ile Glu Ser Glu Gly Gln Ser
            100                 105                 110

Phe Asn Pro Pro Ser Leu Ala Ile Ile Phe Gln Leu Ala Phe Ala Pro
        115                 120                 125

Met Met Gly Arg Thr Thr Asp Leu Ala Val Val Glu Gln Asn Glu Ala
    130                 135                 140

Lys Leu Ala Lys Val Leu Asp Val Tyr Asp Gln Arg Leu Gly Glu Ser
145                 150                 155                 160

Gln Tyr Phe Ala Gly Asp Asp Phe Ser Pro Gly Arg Pro Cys Ala Leu
                165                 170                 175

Ala Gln Cys Arg Phe Pro Cys Glu Gln Asn Gln Gln Gly Trp Leu Asp
            180                 185                 190

His Arg Glu Lys Glu Ser Cys
        195
```

(2) INFORMATION FOR SEQ ID NO:7:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE:  cDNA (iii) HYPOTHETICAL:  NO (iv) ANTI-SENSE:  NO (vi) ORIGINAL SOURCE:
             (F) TISSUE TYPE:  MAIZE (vii) IMMEDIATE SOURCE:
             (B) CLONE:  CC71SE-A.PK0001.G2

(xi) SEQUENCE DESCRIPTION:  SEQ ID NO:7:

```
GCGCGTCGGA GGAGCTCCAC GGCGTCAGGC CCTTCGACCC CGAGCGGACT CCGCTGCTGG     60

CGGCGTGGTC GGAGCGCTTC GGCGCGCTGG ATGCCGTCCA GACGGTGATG CCCGACGTCG    120

GCAGGCTGCT CGAGTTCGGC AAGGCGTTGA TGGCACGTCT GGCGGCTGCG GCCGCCGCCG    180

GTGCAAGCAA TAACTGAAGA GGGCATGGTG TATCCGTCAT GTGTTTCAGG TTTTCGTATA    240

GTGAACAAAA AAGGAAAAAA TAATGCTAGC TACGCATCGG AACGCGGCTT TGTGCTTTGC    300

CGTCTCGCCG TTAGTTCAGC TTATGTGATG TGAGTGTTGC CGTGCATGTG TGTGTTACTT    360

CAGATGTATC CTGTTCGGTT CAGTGATTAT ATGGAACATT TTATTTTGGT TGGATAAAAA    420

AAAAAAAAAA AAAAAAAAAA AAAAAAAAAA AAAAAAA                             458
```

(2) INFORMATION FOR SEQ ID NO:8:

(i) SEQUENCE CHARACTERISTICS:
             (A) LENGTH:  109 amino acids
             (B) TYPE:  amino acid
             (C) STRANDEDNESS: Not Relevant
             (D) TOPOLOGY: Not Relevant (ii) MOLECULE TYPE:  protein (vi) ORIGINAL SOURCE:
             (F) TISSUE TYPE:  MAIZE (vii) IMMEDIATE SOURCE:
             (B) CLONE:  CC71SE-A.PK00001.G2

(xi) SEQUENCE DESCRIPTION:  SEQ ID NO:8:

```
Ala Ser Glu Glu Leu His Gly Val Arg Pro Phe Asp Pro Glu Arg Thr
1               5                   10                  15

Pro Leu Leu Ala Ala Trp Ser Glu Arg Phe Gly Ala Leu Asp Ala Val
            20                  25                  30

Gln Thr Val Met Pro Asp Val Gly Arg Leu Leu Glu Phe Gly Lys Ala
        35                  40                  45

Leu Met Ala Arg Leu Ala Ala Ala Ala Pro Val Gln Ala Ile Thr
50                  55                  60

Glu Glu Gly Met Val Tyr Pro Ser Cys Val Ser Gly Phe Arg Ile Val
65                  70                  75                  80

Asn Lys Lys Gly Lys Asn Asn Ala Ser Tyr Ala Ser Glu Arg Gly Phe
                85                  90                  95

Val Leu Cys Arg Leu Ala Val Ser Ser Ala Tyr Val Met
                100                 105
```

(2) INFORMATION FOR SEQ ID NO:9:

(i) SEQUENCE CHARACTERISTICS:
             (A) LENGTH:  911 base pairs
             (B) TYPE:  nucleic acid
             (C) STRANDEDNESS:  single
             (D) TOPOLOGY:  linear (ii) MOLECULE TYPE:  cDNA (iii) HYPOTHETICAL: NO (iv) ANTI-SENSE: NO (vi) ORIGINAL SOURCE:
            (F) TISSUE TYPE: MAIZE (vii) IMMEDIATE SOURCE:
            (B) CLONE: CC71SE-B.PK0014.B8

(xi) SEQUENCE DESCRIPTION: SEQ ID NO:9:

```
GCAAGGTCGA CATGTCGTCT CCGCCGCCGG TGAAGCTGAT CGGCTTCTTC GGCAGCCCGT    60

ACGCGTTCCG CGCGGAGGCG GCGCTGTGCC TGAAAGGCGT GCCGTACGAG CTGATCCTGG   120

AGGACCTGTT CGGCAGCAAG AGCGAGCTCC TGCTCCACCA CAACCCCGTG CACAAGAAGG   180

TGCCCGTGCT CCTCCACGGC GACGGCCGGG CCATCTCCGA GTCCCTCGTC ATCGCCGAGT   240

ACGTCGACGA GGCCTTCGAC GGGCCGCCGC TGCTCCCCGC CGACCCCTAC GCGCGCGCCG   300

CCGCCCGCTT CTGGGCCGAC TTCATCGAGA CCAGGCTCAC CAAGCCCTTC TTCATGGCGA   360

TCTGGGTGGA GGAGCGCGAC GCGCGGCTGC GGTTCGAGGA GGAGGCCAAG GAGCTCGTGG   420

CGCTGCTGGA GGCGCAGCTC GAGGGAAAGA GGTTCTTCGC CGGCGACAGG CCGGGGTACC   480

TCGACGTGGC CGCGTCCGCG CTCGGGCCCT GGCGCAGCGT CATCGAGGAG CTCAACGGTG   540

TGGCGCTGCT CAGCGAGGAT GACCACCCCA ACCTGTGCCG GTGGACCAGG GACTACTGCG   600

CCTTCGAGGC TCTCAAGCCG TGCATGCCGG ATCGGGAGAA GCTCCTCGCC TACTTCACTA   660

AGAACTTCGA CAGGTACAAG GCGGCCGTCA ATGCGACGCT ATCGCAGTCG CAGCAGTAAT   720

AACTGCCCAA CTGGGTACGC CTCTGCCCGG CCGTATGGCG GGCGTTTCTT TTTTTCTTTC   780

TTCAGAATAA CGTAGCTGTG CCCAGTACTC ATGTTTTCAA TTCTGCAAAG TGCAAACCAA   840

CAAGTCGCTG TGTGGTTTAC TCTTTTTAAA AAAAAAAAA AAAAAAAAAA AAAAAAAAAA   900

AAAAAAAAA A                                                         911
```

(2) INFORMATION FOR SEQ ID NO:10:

(i) SEQUENCE CHARACTERISTICS:
            (A) LENGTH: 235 amino acids
            (B) TYPE: amino acid
            (C) STRANDEDNESS: Not Relevant
            (D) TOPOLOGY: Not Relevant (ii) MOLECULE TYPE: protein (vi) ORIGINAL SOURCE:
            (F) TISSUE TYPE: MAIZE (vii) IMMEDIATE SOURCE:
            (B) CLONE: CC71SE-B.PK0014.B8

(xi) SEQUENCE DESCRIPTION: SEQ ID NO:10:

```
Met Ser Ser Pro Pro Pro Val Lys Leu Ile Gly Phe Phe Gly Ser Pro
1               5                  10                  15

Tyr Ala Phe Arg Ala Glu Ala Ala Leu Cys Leu Lys Gly Val Pro Tyr
            20                  25                  30

Glu Leu Ile Leu Glu Asp Leu Phe Gly Ser Lys Ser Glu Leu Leu Leu
        35                  40                  45

His His Asn Pro Val His Lys Lys Val Pro Val Leu Leu His Gly Asp
    50                  55                  60

Gly Arg Ala Ile Ser Glu Ser Leu Val Ile Ala Glu Tyr Val Asp Glu
65                  70                  75                  80

Ala Phe Asp Gly Pro Pro Leu Leu Pro Ala Asp Pro Tyr Ala Arg Ala
```

```
                   85                 90                 95
Ala Ala Arg Phe Trp Ala Asp Phe Ile Glu Thr Arg Leu Thr Lys Pro
                100                105                110

Phe Phe Met Ala Ile Trp Val Glu Glu Arg Asp Ala Arg Leu Arg Phe
            115                120                125

Glu Glu Glu Ala Lys Glu Leu Val Ala Leu Leu Glu Ala Gln Leu Glu
        130                135                140

Gly Lys Arg Phe Phe Ala Gly Asp Arg Pro Gly Tyr Leu Asp Val Ala
145                150                155                160

Ala Ser Ala Leu Gly Pro Trp Arg Ser Val Ile Glu Glu Leu Asn Gly
                165                170                175

Val Ala Leu Leu Ser Glu Asp Asp His Pro Asn Leu Cys Arg Trp Thr
            180                185                190

Arg Asp Tyr Cys Ala Phe Glu Ala Leu Lys Pro Cys Met Pro Asp Arg
        195                200                205

Glu Lys Leu Leu Ala Tyr Phe Thr Lys Asn Phe Asp Arg Tyr Lys Ala
    210                215                220

Ala Val Asn Ala Thr Leu Ser Gln Ser Gln Gln
225                230                235

(2) INFORMATION FOR SEQ ID NO:11:

(i) SEQUENCE CHARACTERISTICS:
        (A) LENGTH:  948 base pairs
        (B) TYPE:  nucleic acid
        (C) STRANDEDNESS:  single
        (D) TOPOLOGY:  linear (ii) MOLECULE TYPE: cDNA (iii) HYPOTHETICAL: NO (iv) ANTI-SENSE: NO (vi) ORIGINAL SOURCE:
         (F) TISSUE TYPE: maize (vii) IMMEDIATE SOURCE:
          (B) CLONE: ceb5.pk0051.f8

(xi) SEQUENCE DESCRIPTION: SEQ ID NO:11:

AGCGCATGCA GGTAGCAATG GCGGGGGAGA CGAAGAAGGG CCTGGTGCTG CTGGACTTCT     60

GGGTGAGCCC GTTCGGGCAG CGCTGCCGCA TCGCGCTGGC GGAGAAGGGC ATCGCCTACG    120

AGTACTCGGA GCAGGAGCTG CTGGGCGGCG CCAAGAGCGA CATCCTCCTC CGCTCCAACC    180

CGGTGCACAA GAAGATCCCC GTGCTCCTCC ACGACGGCCG CCCCGTCTGC GAGTCCCTCG    240

TCATCCTCGA GTACCTCGAG GAGGCCTTCC CGGAGGCCTC CCCCAGGCTG CTCCCCGACG    300

CCGCCTACGC GCGCGCGCAG GCCCGCTTCT GGGCGGCCTA CTCCGACAAG GTCTACAAGG    360

CCGGCACGCG GCTGTGGAAG CTCAGGGGCG ACGCGCGGGC GCAGGCGCGC GCCGAGATCG    420

TGCAGGTGGT CCGGAACCTC GACGGCGAGC TAGGGGACAA GGCCTTCTTC GGCGGCGAGG    480

CGTTCGGGTT CGTGGACGTG GCGCTCGTGC CCTTCGTGCC GTGGCTCCCC AGCTACGAGC    540

GGTACGGGGA CTTCAGCGTG GCGGAGATCG CGCCCAGGCT GGCGGCGTGG GCGCGCCGGT    600

GCGCGCAGCG GGAGAGCGTG GCCAGGACCC TTCACCCGCC GGAAAAGGTG GACGAGTTCA    660

TCAACCTGCT CAAGAAGACC TACGGCATCG AGTAGTAGAG CGGACTACTA CTAGCAGAGG    720

AGATGGTACC GGCCGTACGT ACGTGGCTGC CATGCAGTTT TTGTTTCGGT TTGTTTAAAC    780

GGGACTCCAT GAATGGATGG AACTCTTCTT GGGCTCCGTG TGCTACATAC ACATCTGTAA    840
```

```
AGGTGAACTA AAATCACGGT AAAAACTCGG AAATTAGTTT GTAAAGGGTC CAGCCCCCCT         900

CCTTTATAAA TAGAGAGGTA TACGGCTGAT AAAAAAAAAA AAAAAAA                      948
```

(2) INFORMATION FOR SEQ ID NO:12:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: maize (vii) IMMEDIATE SOURCE:
        (B) CLONE: ceb5.pk0051.f8

(xi) SEQUENCE DESCRIPTION: SEQ ID NO:12:

```
Met Ala Gly Glu Thr Lys Lys Gly Leu Val Leu Leu Asp Phe Trp Val
 1               5                  10                  15

Ser Pro Phe Gly Gln Arg Cys Arg Ile Ala Leu Ala Glu Lys Gly Ile
                20                  25                  30

Ala Tyr Glu Tyr Ser Glu Gln Glu Leu Leu Gly Gly Ala Lys Ser Asp
            35                  40                  45

Ile Leu Leu Arg Ser Asn Pro Val His Lys Lys Ile Pro Val Leu Leu
50                  55                  60

His Asp Gly Arg Pro Val Cys Glu Ser Leu Val Ile Leu Glu Tyr Leu
65                  70                  75                  80

Glu Glu Ala Phe Pro Glu Ala Ser Pro Arg Leu Leu Pro Asp Ala Ala
                85                  90                  95

Tyr Ala Arg Ala Gln Ala Arg Phe Trp Ala Ala Tyr Ser Asp Lys Val
            100                 105                 110

Tyr Lys Ala Gly Thr Arg Leu Trp Lys Leu Arg Gly Asp Ala Arg Ala
        115                 120                 125

Gln Ala Arg Ala Glu Ile Val Gln Val Val Arg Asn Leu Asp Gly Glu
    130                 135                 140

Leu Gly Asp Lys Ala Phe Phe Gly Gly Glu Ala Phe Gly Phe Val Asp
145                 150                 155                 160

Val Ala Leu Val Pro Phe Val Pro Trp Leu Pro Ser Tyr Glu Arg Tyr
                165                 170                 175

Gly Asp Phe Ser Val Ala Glu Ile Ala Pro Arg Leu Ala Ala Trp Ala
            180                 185                 190

Arg Arg Cys Ala Gln Arg Glu Ser Val Ala Arg Thr Leu His Pro Pro
        195                 200                 205

Glu Lys Val Asp Glu Phe Ile Asn Leu Leu Lys Lys Thr Tyr Gly Ile
    210                 215                 220

Glu
225
```

(2) INFORMATION FOR SEQ ID NO:13:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (F) TISSUE TYPE: MAIZE (vii) IMMEDIATE SOURCE:
         (B) CLONE: CR1N.PK0003.B1

(xi) SEQUENCE DESCRIPTION: SEQ ID NO:13:

```
GTTGGGGATG TGGGCGAGCC CTATGGTGAT CAGGGTGGAG TGGGCGCTGC GGCTGAAGGG      60
CGTCGAGTAC GAGTACGTCG ACGAGGACCT CGCCAACAAG AGCGCCGACC TGCTCCGCCA     120
CAACCCGGTG ACCAAGAAGG TGCCCGTGCT CGTCCACGAC GGCAAGCCGG TCGCGGAGTC     180
CACCATCATC GTCGAGTACA TCGACGAGGT CTGGAAGGGC GGCTACCCCA TCATGCCGGG     240
CGACCCCTAC GAGCGTGCCC AGGCAAGGTT CTGGGCCAGG TTCGCTGAAG ACAAGTGCAA     300
CGCTGCTCTG TACCCGATCT TCACCGCGAC CGGCGAGGCG CAGCGCAAGG CGGTGCACGA     360
GGCCCAGCAG TGCCTCAAGA CCCTGGAGAC GGCCTTGGAC GGGAAGAAGT TCTTCGGCGG     420
GGACGCCGTG GGCTACCTCG ACATCGTCGT CGGGTGGTTC GCGCACTGGC TCCCCGTCAT     480
CGAGGAGGTG ACCGGCGCCA GCGTCGTCAC CGACGAGGAG CTGCCGCTGA TGAAGGCCTG     540
GTTCGGCCGG TTCCTCGCCG TTGACGTGGT GAAGGCGGCC CTGCCCGACA GGGACAGGCT     600
CCTCGCCGCC AACAAGGCCC GCCGTGAGCA GCTCCTCTCC GCGTAGATGG CTAGTAATTC     660
TGGAGCAGCT AGTTTCACCG CCGACGCTCA TATATTGCTG AATAAGGACT GGTTGCACTT     720
TTGCACGTTG TGCAGTGCAG CCGAGGTTTG GATGACCTCT GCCCCTCTGT TCCATTTCAG     780
AATGGTAGTC CCATAATAAT GCATATACAT CATGCATAAA AAAAAAAAAA AAAAAAAAA     840
```

(2) INFORMATION FOR SEQ ID NO:14:

(i) SEQUENCE CHARACTERISTICS:
        (A) LENGTH: 212 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
         (F) TISSUE TYPE: MAIZE (vii) IMMEDIATE SOURCE:
         (B) CLONE: CR1N.PK0003.B1

(xi) SEQUENCE DESCRIPTION: SEQ ID NO:14:

```
Met Trp Ala Ser Pro Met Val Ile Arg Val Glu Trp Ala Leu Arg Leu
1               5                   10                  15

Lys Gly Val Glu Tyr Glu Tyr Val Asp Glu Asp Leu Ala Asn Lys Ser
            20                  25                  30

Ala Asp Leu Leu Arg His Asn Pro Val Thr Lys Lys Val Pro Val Leu
        35                  40                  45

Val His Asp Gly Lys Pro Val Ala Glu Ser Thr Ile Ile Val Glu Tyr
    50                  55                  60

Ile Asp Glu Val Trp Lys Gly Tyr Pro Ile Met Pro Gly Asp Pro
65                  70                  75                  80

Tyr Glu Arg Ala Gln Ala Arg Phe Trp Ala Arg Phe Ala Glu Asp Lys
                85                  90                  95

Cys Asn Ala Ala Leu Tyr Pro Ile Phe Thr Ala Thr Gly Glu Ala Gln
            100                 105                 110

Arg Lys Ala Val His Glu Ala Gln Gln Cys Leu Lys Thr Leu Glu Thr
```

```
         115                 120                 125
    Ala Leu Asp Gly Lys Lys Phe Phe Gly Gly Asp Ala Val Gly Tyr Leu
        130                 135                 140

Asp Ile Val Val Gly Trp Phe Ala His Trp Leu Pro Val Ile Glu Glu
    145                 150                 155                 160

Val Thr Gly Ala Ser Val Val Thr Asp Glu Glu Leu Pro Leu Met Lys
                    165                 170                 175

Ala Trp Phe Gly Arg Phe Leu Ala Val Asp Val Lys Ala Ala Leu
                180                 185                 190

Pro Asp Arg Asp Arg Leu Leu Ala Ala Asn Lys Ala Arg Arg Glu Gln
                195                 200                 205

Leu Leu Ser Ala
        210

(2) INFORMATION FOR SEQ ID NO:15:

(i) SEQUENCE CHARACTERISTICS:
        (A) LENGTH: 861 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (F) TISSUE TYPE: MAIZE (vii) IMMEDIATE SOURCE:
          (B) CLONE: CR1N.PK0014.G8

(xi) SEQUENCE DESCRIPTION: SEQ ID NO:15:

CGGAGGCGCA GAGCTTCGAC GCGCCCAGCG CCGAGATGGT CTACAGCCTC GCCTTCCTGC    60

CGCCCACCCT GCCCAAGCAG AACGACAACG GCAACGGCGG CGCGTTCAAC GCCAGGGACG   120

CCACCGTAGG CAGCAACGCC GACGCGTCCA GCGGCAAGCG CGGTGTGGCC GGGTCACAGC   180

CGGCGGCGAG CCAGACCAAG GTGAGCGCGC AGAAGGAGGA GGAGATGCTG AAGCTGTTCG   240

AGCAGAGGAA GAAGGACCTG GAGAAGCTGC TGGACATCTA CGAGCAGCGC CTGGAGGAGG   300

CCACGTTCCT GGCCGGCGAC AACTTCACCA TCGCCGACCT GTCGCACCTG CCCTACGCGG   360

ACCACCTCGT CTCCGACCCG CGCTCCCGCC GCATGTTCGA GTCCCGCAAG AACGTCAGCA   420

GGTGGTGGCA CGACGTCTCC GGCCGCGACA CCTGGAAGTA CGTCAAGACC CTGCAGCGCC   480

CGCCGTCCAC GTCCACCGAC GCCAGCGCCA AGAACGGCCA GCTGGGCCAG CAGCAGCACC   540

TGCCGTCGTC CACCGACGGC CACGGCGTGA AGACCCAACG GCTGGTCCAG AACGAGCGGC   600

ACTTCTAGCT GTTGCCGTCC CTTCCCGCCG ACGAATAAAC TACCTGCGCC GCCGCCACCG   660

CCGCCATCCA TCAACATGGT TCCTTGTGCT GTTCGTGTCG TTTTCATACG TCATACGTGT   720

CTTGCTGCTT TTGAAGCTCC GTTCCCGGGT GCAGGGACCT ACGAGTCCAT TCCGTCGTTT   780

GCTGATTCTG TTCGTCGTGT AATAAAATGA AAACCCCACC CCGTTTTGAA TGAAAAAAAA   840

AAAAAAAAAA AAAAAAAAA A                                              861

(2) INFORMATION FOR SEQ ID NO:16:

(i) SEQUENCE CHARACTERISTICS:
        (A) LENGTH: 190 amino acids
        (B) TYPE: amino acid
        (C) STRANDEDNESS: Not Relevant
```

(D) TOPOLOGY: Not Relevant (ii) MOLECULE TYPE: protein (vi) ORIGINAL SOURCE:
         (F) TISSUE TYPE: maize (vii) IMMEDIATE SOURCE:
         (B) CLONE: crln.pk0014.g8

(xi) SEQUENCE DESCRIPTION: SEQ ID NO:16:

Met Val Tyr Ser Leu Ala Phe Leu Pro Pro Thr Leu Pro Lys Gln Asn
1               5                  10                  15

Asp Asn Gly Asn Gly Gly Ala Phe Asn Ala Arg Asp Ala Thr Val Gly
            20                  25                  30

Ser Asn Ala Asp Ala Ser Ser Gly Lys Arg Gly Val Ala Gly Ser Gln
        35                  40                  45

Pro Ala Ala Ser Gln Thr Lys Val Ser Ala Gln Lys Glu Glu Glu Met
    50                  55                  60

Leu Lys Leu Phe Glu Gln Arg Lys Lys Asp Leu Glu Lys Leu Leu Asp
65              70                  75                  80

Ile Tyr Glu Gln Arg Leu Glu Glu Ala Thr Phe Leu Ala Gly Asp Asn
                85                  90                  95

Phe Thr Ile Ala Asp Leu Ser His Leu Pro Tyr Ala Asp His Leu Val
            100                 105                 110

Ser Asp Pro Arg Ser Arg Arg Met Phe Glu Ser Arg Lys Asn Val Ser
        115                 120                 125

Arg Trp Trp His Asp Val Ser Gly Arg Asp Thr Trp Lys Tyr Val Lys
    130                 135                 140

Thr Leu Gln Arg Pro Pro Ser Thr Ser Thr Asp Ala Ser Ala Lys Asn
145                 150                 155                 160

Gly Gln Leu Gly Gln Gln Gln His Leu Pro Ser Ser Thr Asp Gly His
                165                 170                 175

Gly Val Lys Thr Gln Arg Leu Val Gln Asn Glu Arg His Phe
            180                 185                 190

(2) INFORMATION FOR SEQ ID NO:17:

(i) SEQUENCE CHARACTERISTICS:
         (A) LENGTH: 917 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (F) TISSUE TYPE: MAIZE (vii) IMMEDIATE SOURCE:
         (B) CLONE: M.15.5.D06.SK20

(xi) SEQUENCE DESCRIPTION: SEQ ID NO:17:

ATGGCGGAGG TGGAGGCGAC GGTGGGGCGA CTGATGCTGT ACTCGTACTG GCGCAGCTCG      60

TGCTCCCACC GTGCCCGCAT CGCTCTCAAT CTCAAAGGTG TGGATTACGA GTACAAGGCG     120

GTGAACCTTC TCAAGGGCGA GCAGTCTGAT CCAGAATTCG TCAAGCTTAA TCCTATGAAG     180

TTCGTCCCTG CGTTGGTTGA TGGCAGTTCT GTAATAGGTG ACTCTTACGC GATAACACTG     240

TATTTGGAGG ACAAGTACCC AGAGCCTCCT CTTCTACCTC AAGACCTTCA AAAGAAAGCT     300

```
TTGAATCACC AGATTGCAAG CATTGTAGCT TCTGGTATTC AACCTCTCCA TAACCTCACA      360

GTGTTGAGGT TCATTGACCA GAAGGTTGGT GCAGGGGAGA GTGTGTTGTG GACTCAACAA      420

CAAATCGAGA GAGGTTTCAC AGCTATTGAG AACCTGATCA AACTAAAAGG ATGCGCCGGG      480

AAGTATGCAA CAGGAGATGA AGTCCAACTG GCAGATGTAT TCCTTGCACC CCAGATCTAT      540

GCAGCCATTG AACGCACTAA AATTGACATG TCAAACTACC TCACTCTTGC TAGGCTCCAC      600

TCGGAGTACA TGTCACACCC TGCGTTTGAA GCAGCGCTCC CTGGCAAGCA ACCGGACGCC      660

CCTTCATCCT CCTAGGAACT GCACCCTAGT GTGTTGTTCC TCTGAATATA TATATATATA      720

TATGTATACT TCTGTAAGAA TTAATAATTA CAGAGTTTCG TCTGCTATGT CGAAAAATGT      780

CAAAAGTTTT TGTGATTTCA GAGACTAGCG GCATGAAGCG TCGTTGTGGA TCTGGCCGTC      840

GTCCTCATGT GGCATCTGTG ATTTCAGGGC ATGCACTTCG TCTTAGAAGG GAAAAAAAAA      900

AAAAAAAAAA AAAAAA                                                     917
```

(2) INFORMATION FOR SEQ ID NO:18:

(i) SEQUENCE CHARACTERISTICS:
        (A) LENGTH: 224 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (B) CLONE: M.15.5.D06.SK20

(xi) SEQUENCE DESCRIPTION: SEQ ID NO:18:

```
Met Ala Glu Val Glu Ala Thr Val Gly Arg Leu Met Leu Tyr Ser Tyr
1               5                   10                  15

Trp Arg Ser Ser Cys Ser His Arg Ala Arg Ile Ala Leu Asn Leu Lys
            20                  25                  30

Gly Val Asp Tyr Glu Tyr Lys Ala Val Asn Leu Leu Lys Gly Glu Gln
        35                  40                  45

Ser Asp Pro Glu Phe Val Lys Leu Asn Pro Met Lys Phe Val Pro Ala
    50                  55                  60

Leu Val Asp Gly Ser Ser Val Ile Gly Asp Ser Tyr Ala Ile Thr Leu
65                  70                  75                  80

Tyr Leu Glu Asp Lys Tyr Pro Glu Pro Pro Leu Leu Pro Gln Asp Leu
                85                  90                  95

Gln Lys Lys Ala Leu Asn His Gln Ile Ala Ser Ile Val Ala Ser Gly
            100                 105                 110

Ile Gln Pro Leu His Asn Leu Thr Val Leu Arg Phe Ile Asp Gln Lys
        115                 120                 125

Val Gly Ala Gly Glu Ser Val Leu Trp Thr Gln Gln Ile Glu Arg
    130                 135                 140

Gly Phe Thr Ala Ile Glu Asn Leu Ile Gln Leu Lys Gly Cys Ala Gly
145                 150                 155                 160

Lys Tyr Ala Thr Gly Asp Glu Val Gln Leu Ala Asp Val Phe Leu Ala
                165                 170                 175

Pro Gln Ile Tyr Ala Ala Ile Glu Arg Thr Lys Ile Asp Met Ser Asn
            180                 185                 190

Tyr Leu Thr Leu Ala Arg Leu His Ser Glu Tyr Met Ser His Pro Ala
        195                 200                 205
```

```
Phe Glu Ala Ala Leu Pro Gly Lys Gln Pro Asp Ala Pro Ser Ser Ser
    210                 215                 220
```

(2) INFORMATION FOR SEQ ID NO:19:

(i) SEQUENCE CHARACTERISTICS:
        (A) LENGTH: 919 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (F) TISSUE TYPE: MAIZE (vii) IMMEDIATE SOURCE:
        (B) CLONE: CR1N.PK0040.E12

(xi) SEQUENCE DESCRIPTION: SEQ ID NO:19:

```
CACCTGCTGT ATCTCATTAC CATCTGCATC TGGTTGCCCG TTGATTGAGA AGGAGGAGCT    60

GAGGGCCATG GCGACCGAGA AGCCCATCCT GTACAACGCC TGGATCAGCT CCTGCTCCCA   120

CCGTGTTCGC ATCGCACTCA ACCTCAAAGG TGTGGATTAC GAGTACAAGT CGGTAAACCC   180

TAGGACAGAT CCAGATTATG AAAAAATCAA TCCAATCAAA TATATTCCAG CATTAGTAGA   240

TGGGGACATA GTCGTTTCTG ATTCTCTTGC CATCTCATTG TATTTGGAAG ATAAGTATCC   300

TGAGCATCCA CTCCTGCCTA AGATCTCAA GAGGAAAGCT CTTAATCTTC AGATTGCAAA    360

CATTGTTTGT TCAAGCATTC AACCTCTTCA AGGCTATGCT GTTATTGGTC TGCACGAGGG   420

TAGGATGAGC CCAGATGAGG GCCTTCATAT TGTTCAAAGT TATATTGACA AGGGATTCAG   480

AGCGATCGAA AAGCTGTTGG AAGGATGTGA GAGTAAATAT GCTACTGGAG ATGATGTCCA   540

ATTGGCAGAT GTGTTCCTTG AACCACAGAT ACATGCCGGC ATAAATCGCT TCCAAATCGA   600

TATGTCGATG TACCCAATCT GGAGAGGCT CCATGATGCA TACATGCAAA TTCCCGCATT    660

CCAAGCCGCG CTTCCTAAAA ATCAACCAGA CGCACCTTCA TCATAATCAT CAAGATTATC   720

TCAATAATTT GCATGTCATT TTGTAATAAT TTGGATAGGG AGCCACTGCT TCCTCCATCC   780

CGTTGTGGAT CAAAAGGGTG AACGATTGGC ACTTACCTGC ATGGTCCAAT ACCTATTATA   840

TTTCTTAAAC AGATACTATT TACGGCTATT GTAATTTAAG CCCAAAAAAA AAAAAAAAA    900

AAAAAAAAAA AAAAAAAA                                                 919
```

(2) INFORMATION FOR SEQ ID NO:20:

(i) SEQUENCE CHARACTERISTICS:
        (A) LENGTH: 212 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (B) CLONE: CR1N.PK0040.E12

(xi) SEQUENCE DESCRIPTION: SEQ ID NO:20:

```
Met Ala Thr Glu Lys Pro Ile Leu Tyr Asn Ala Trp Ile Ser Ser Cys
1               5                   10                  15
```

```
Ser His Arg Val Arg Ile Ala Leu Asn Leu Lys Gly Val Asp Tyr Glu
         20                  25                  30

Tyr Lys Ser Val Asn Pro Arg Thr Asp Pro Asp Tyr Glu Lys Ile Asn
         35                  40                  45

Pro Ile Lys Tyr Ile Pro Ala Leu Val Asp Gly Asp Ile Val Val Ser
         50                  55                  60

Asp Ser Leu Ala Ile Ser Leu Tyr Leu Glu Asp Lys Tyr Pro Glu His
 65                  70                  75                  80

Pro Leu Leu Pro Lys Asp Leu Lys Arg Lys Ala Leu Asn Leu Gln Ile
                 85                  90                  95

Ala Asn Ile Val Cys Ser Ser Ile Gln Pro Leu Gln Gly Tyr Ala Val
                100                 105                 110

Ile Gly Leu His Glu Gly Arg Met Ser Pro Asp Glu Gly Leu His Ile
                115                 120                 125

Val Gln Ser Tyr Ile Asp Lys Gly Phe Arg Ala Ile Glu Lys Leu Leu
                130                 135                 140

Glu Gly Cys Glu Ser Lys Tyr Ala Thr Gly Asp Asp Val Gln Leu Ala
145                 150                 155                 160

Asp Val Phe Leu Glu Pro Gln Ile His Ala Gly Ile Asn Arg Phe Gln
                165                 170                 175

Ile Asp Met Ser Met Tyr Pro Ile Leu Glu Arg Leu His Asp Ala Tyr
                180                 185                 190

Met Gln Ile Pro Ala Phe Gln Ala Leu Pro Lys Asn Gln Pro Asp
                195                 200                 205

Ala Pro Ser Ser
    210

(2) INFORMATION FOR SEQ ID NO:21:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (F) TISSUE TYPE: MAIZE (vii) IMMEDIATE SOURCE:
         (B) CLONE: CEB5.PK0049.A11

(xi) SEQUENCE DESCRIPTION: SEQ ID NO:21:

CATCGATCCG CCATTGCTCA CCGCACAAGT GCACGCTCAC CTCACACACG CAGCTAAGTA      60

GCTAACGCCG TAGGCGAGAA CAAGAAAAGG CTCGACATGG CCGAGGAGAA GAAGCAGGGC     120

CTGCAGCTGC TGGACTTCTG GGTGAGCCCA TTCGGGCAGC GCTGCCGCAT CGCGCTGGAC     180

GAGAAGGGCC TGGCCTACGA GTACCTGGAG CAGGACCTGA GGAACAAGAG CGAGCTGCTC     240

CTCCGCGCCA ACCCGGTGCA CAAGAAGATC CCCGTGCTGC TGCACGACGG CCGCCCCGTC     300

TGCGAGTCCC TCGTCATCGT GCAGTACCTC GACGAGGCGT TCCCGGAGGC GGCGCCGGCG     360

CTGCTCCCCG CCGACCCCTA CGCGCGCGCG CAGGCCCGCT TCTGGGCGGA CTACGTCGAC     420

AAGAAGCTGT ACGACTGCGG CACCCGGCTG TGGAAGCTCA AGGGGACGG CCAGGCGCAG     480

GCGCGCGCCG AGATGGTCGA GATCCTCCGC ACGCTGGAGG GCGCGCTCGG CGACGGGCCC     540
```

```
TTCTTCGGTG GCGACGCCCT CGGCTTCGTC GACGTCGCGC TCGTGCCCTT CACGTCCTGG        600

TTCCTCGCCT ACGACCGCTT CGGCGGCGTC AGCGTGGAGA AGGAGTGCCC GAGGCTGGCC        660

GCCTGGGCCA AGCGCTGCGC CGAGCGCCCC AGCGTCGCCA AGAACCTCTA CCCGCCCGAG        720

AAGGTCTACG ACTTCGTCTG CGGGATGAAG AAGAGGCTGG GCATCGAGTA GAGCATCCAT        780

CGGTCGGCCG GTGGCTGGCC GGGAGTAATA ATGACGAACC AATAATCTAG TTTTGGTTTT        840

AGTGTGCTCA GCAGAGCAGT TCGTGTTCAT GAGTTCGTCG TCGTTGTATT TTCTATTGTC        900

AGCGGTGGCA GCGCCGTACG TGTTGCCTCG TACACCACAA CCGAATAAAT GGTTATGAAT        960

TTCTTCTTGT TGTCTTAAAA AAAAAAAAAA AAAAAA                                 996
```

(2) INFORMATION FOR SEQ ID NO:22:

(i) SEQUENCE CHARACTERISTICS:
        (A) LENGTH: 224 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (B) CLONE: CEB5.PK0049.A11

(xi) SEQUENCE DESCRIPTION: SEQ ID NO:22:

```
Met Ala Glu Glu Lys Lys Gln Gly Leu Gln Leu Leu Asp Phe Trp Val
1               5                  10                  15

Ser Pro Phe Gly Gln Arg Cys Arg Ile Ala Leu Asp Glu Lys Gly Leu
            20                  25                  30

Ala Tyr Glu Tyr Leu Glu Gln Asp Leu Arg Asn Lys Ser Glu Leu Leu
        35                  40                  45

Leu Arg Ala Asn Pro Val His Lys Lys Ile Pro Val Leu Leu His Asp
    50                  55                  60

Gly Arg Pro Val Cys Glu Ser Leu Val Ile Val Gln Tyr Leu Asp Glu
65                  70                  75                  80

Ala Phe Pro Glu Ala Ala Pro Ala Leu Leu Pro Ala Asp Pro Tyr Ala
                85                  90                  95

Arg Ala Gln Ala Arg Phe Trp Ala Asp Tyr Val Asp Lys Lys Leu Tyr
            100                 105                 110

Asp Cys Gly Thr Arg Leu Trp Lys Leu Lys Gly Asp Gly Gln Ala Gln
        115                 120                 125

Ala Arg Ala Glu Met Val Glu Ile Leu Arg Thr Leu Glu Gly Ala Leu
    130                 135                 140

Gly Asp Gly Pro Phe Phe Gly Gly Asp Ala Leu Gly Phe Val Asp Val
145                 150                 155                 160

Ala Leu Val Pro Phe Thr Ser Trp Phe Leu Ala Tyr Asp Arg Phe Gly
                165                 170                 175

Gly Val Ser Val Glu Lys Glu Cys Pro Arg Leu Ala Ala Trp Ala Lys
            180                 185                 190

Arg Cys Ala Glu Arg Pro Ser Val Ala Lys Asn Leu Tyr Pro Pro Glu
        195                 200                 205

Lys Val Tyr Asp Phe Val Cys Gly Met Lys Lys Arg Leu Gly Ile Glu
    210                 215                 220
```

(2) INFORMATION FOR SEQ ID NO:23:

(i) SEQUENCE CHARACTERISTICS:
    (A) LENGTH: 895 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (F) TISSUE TYPE: MAIZE (vii) IMMEDIATE SOURCE:
    (B) CLONE: CS1.PK0059.E2

(xi) SEQUENCE DESCRIPTION: SEQ ID NO:23:

```
GGCACGAGAC GACATCGAAG GAGCCTGCGA AGCGAGCGAG AGTCTATAAT GGCGGACGGA   60
GGCGAGCTGC AGCTGCTGGG CTCATGGTAC AGCCCCTACG TGATCCGCGC CAAGGTGGCG  120
CTGGGGCTGA AGGGGCTCAG CTACGAGTTC GTCGAGGAGG ACCTCTCCCG CAAGAGCGAC  180
CTGCTGCTGA AGCTCAACCC GGTGCACAGG AAGGTGCCCG TGCTGGTCCA CGGCGGCCGC  240
CCCGTGTGCG AGTCGCTCGT CATCCTGCAG TACGTCGACG AGACCTGGGC AGGCACCGGG  300
ACCCCTCTCC TCCCCGCCGA CGCCTACGAC CGCGCCATGG CTCGCTTCTG GGCAGCCTAC  360
GTCGACGACA AGTTCTACAA GGAGTGGAAC CGGCTGTTCT GGTCGACGAC GGCGGAGAAG  420
GCGGCGGAGG CGCTCGGCGT CGTCGTCCCC GTGGTGGAGA CGCTGGAGCA GGCGTTCAGG  480
GAGTGCTCCA AAGGGAAACC TTCTTCGGCG GCGACGCCGT CGGGCTCGTG GACATCGCGC  540
TCGGGAGCTT CGTGGTGTGG ATCAGGGTGG TGGACGAGGC GGCCGGCGTA AAGCTTCTGG  600
ACGAGGCCAA GTTCCCGGCC TTGACGGCGT GGGCGGAGCG CTTCTTGGCG GTGGACGCCG  660
TGAAGGAGGT GATGCCGGAC GCCGGAAGGC TGTTGGAGCA CTACAAGGGG TTTCTGGCTA  720
AACGGTCTCC ACCTGCTGGT TACTGAACGC TGTAACTGTA AGCCTGTAAC AGCAAGCTCA  780
GTGTTCGTGT ACTTTTCCGT GCGTTAACGT GTACTAGAGT TCAGGAAAGG CTTTGATTCT  840
GTCCAGAGTC CAGACGAATA AACGAATGTT TTTTATAAAA AAAAAAAAAA AAAAA       895
```

(2) INFORMATION FOR SEQ ID NO:24:

(i) SEQUENCE CHARACTERISTICS:
        (A) LENGTH: 180 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (F) TISSUE TYPE: MAIZE (vii) IMMEDIATE SOURCE:
        (A) LIBRARY: CS1.PK0059.E2

(xi) SEQUENCE DESCRIPTION: SEQ ID NO:24:

```
Met Ala Asp Gly Gly Glu Leu Gln Leu Leu Gly Ser Trp Tyr Ser Pro
1               5                  10                  15

Tyr Val Ile Arg Ala Lys Val Ala Leu Gly Leu Lys Gly Leu Ser Tyr
                20                  25                  30

Glu Phe Val Glu Glu Asp Leu Ser Arg Lys Ser Asp Leu Leu Leu Lys
            35                  40                  45

Leu Asn Pro Val His Arg Lys Val Pro Val Leu Val His Gly Gly Arg
```

-continued

```
            50                  55                  60
Pro Val Cys Glu Ser Leu Val Ile Leu Gln Tyr Val Asp Glu Thr Trp
 65                  70                  75                  80

Ala Gly Thr Gly Thr Pro Leu Leu Pro Ala Asp Ala Tyr Asp Arg Ala
                 85                  90                  95

Met Ala Arg Phe Trp Ala Ala Tyr Val Asp Asp Lys Phe Tyr Lys Glu
                100                 105                 110

Trp Asn Arg Leu Phe Trp Ser Thr Thr Ala Glu Lys Ala Ala Glu Ala
            115                 120                 125

Leu Gly Val Val Val Pro Val Val Glu Thr Leu Glu Gln Ala Phe Arg
        130                 135                 140

Glu Cys Ser Lys Gly Lys Pro Ser Ser Ala Ala Thr Pro Ser Gly Ser
145                 150                 155                 160

Trp Thr Ser Arg Ser Gly Ala Ser Trp Cys Gly Ser Gly Trp Trp Thr
                165                 170                 175

Arg Arg Pro Ala
            180
```

MAIZE GLUTATHIONE-S-TRANSFERASE ENZYMES

FIELD OF THE INVENTION

This invention is in the field of plant molecular biology. More specifically, this invention pertains to nucleic acid fragments encoding maize glutathione-S-transferase (GST) enzymes involved in the detoxification of xenobiotic compounds in plants and seeds.

BACKGROUND OF THE INVENTION

Glutathione-S-transferases (GST) are a family of enzymes which catalyze the conjugation of glutathione, homoglutathione (hGSH) and other glutathione-like analogs via a sulfhydryl group, to a large range of hydrophobic, electrophilic compounds. The conjugation can result in detoxification of these compounds. GST enzymes have been identified in a range of plants including maize (Wosnick et al., *Gene* (Amst) 76 (1) (1989) 153–160; Rossini et al., *Plant Physiology* (Rockville) 112 (4) (1996) 1595–1600; Holt et al., *Planta* (Heidelberg) 196 (2) (1995) 295–302), wheat (Edwards et al., *Pestic. Biochem. Physiol.* (1996) 54(2), 96–104), sorghum (Hatzios et al., *J. Environ. Sci. Health*, Part B (1996), B31(3), 545–553), arabidopsis (Van Der Kop et al., *Plant Molecular Biology* 30 (4) (1996), sugarcane (Singhal et al., *Phytochemistry* (OXF) 30 (5) (1991) 1409–1414), soybean (Flury et al., *Physiologia Plantarum* 94 (1995) 594–604) and peas (Edwards R., *Physiologia Plantarum* 98 (3) (1996) 594–604). GST's can comprise a significant portion of total plant protein, for example attaining from 1 to 2% of the total soluble protein in etiolated maize seedlings (Timmermann, *Physiol Plant.* (1989) 77(3), 465–71).

Glutathione S-transferases (GSTs; EC 2.5.1.18) catalyze the nucleophilic attack of the thiol group of GSH to various electrophilic substrates. Their functions and regulation in plants has been recently reviewed (Marrs et al., *Annu Rev Plant Physiol Plant Mol Biol* 47:127–58 (1996); Droog, F. *J Plant Growth Regul* 16:95–107, (1997)). They are present at every stage of plant development from early embryogenesis to senescence and in every tissue class examined. The agents that have been shown to cause an increase in GST levels have the potential to cause oxidative destruction in plants, suggesting a role for GSTs in the protection from oxidative damage. In addition to their role in the protection from oxidative damage, GSTs have the ability to nonenzymatically bind certain small molecules, such as auxin (Zettl et al., *PNAS* 91:689–693, (1994)) and perhaps regulate their bioavailability. Furthermore the addition of GSH to a molecule serves as an "address" to send that molecule to the plant vacuole (Marrs et al., *Nature* 375:397–400, (1995)).

GSTs have also been implicated in the detoxification of certain herbicides. Maize GSTs have been well characterized in relation to herbicide metabolism. Three genes from maize have been cloned: GST 29 (Shah et al., *Plant Mol Biol* 6, 203–211 (1986)), GST 27 (Jepson et al., *Plant Mol Biol* 26:1855–1866, (1994)), GST 26 (Moore et al., *Nucleic Acids Res* 14:7227–7235 (1986)). These gene products form four GST isoforms: GST I (a homodimer of GST 29), GST II (a heterodimer of GST 29 and GST 27), GST III (a homodimer of GST 26), and GST IV (a homodimer of GST 27). GST 27 is highly inducible by safener compounds (Jepson (1994) supra; Holt et al., *Planta* 196:295–302, (1995)) and overexpression of GST 27 in tobacco confers alachlor resistance to transgenic tobacco (Jepson, personal communication). Additionally, Bridges et al. (U.S. Pat. No. 5,589,614) disclose the sequence of a maize derived GST isoform II promoter useful for the expression of foreign genes in maize and wheat. In soybean, herbicide compounds conjugated to hGSH have been detected and correlated with herbicide selectivity (Frear et al., *Physiol* 20: 299–310 (1983); Brown et al., *Pest Biochem Physiol* 29:112–120, (1987)). This implies that hGSH conjugation is an important determinant in soybean herbicide selectivity although this hypothesis has not been characterized on a molecular level.

Some efforts have been made to alter plant phenotypes by the expression of either plant or mammalian foreign GST genes or their promoters in mature plant tissue. For example, Helmer et al. (U.S. Pat. No. 5,073,677) teach the expression of a rat GST gene in tobacco under the control of a strong plant promoter. Similarly, Jepson et al. (WO 97/11189) disclose a chemically inducible maize GST promoter useful for the expression of foreign proteins in plants; Chilton et al. (EP 256223) discuss the construction of herbicide tolerant plants expressing a foreign plant GST gene; and Bieseler et al. (WO 96/23072) teach DNA encoding GSTIIIc, its recombinant production and transgenic plants containing the DNA having a herbicide-tolerant phenotype.

Manipulation of nucleic acid fragments encoding soybean GST to use in screening in assays, the creation of herbicide-tolerant transgenic plants, and altered production of GST enzymes depend on the heretofore unrealized isolation of nucleic acid fragments that encode all or a substantial portion of a soybean GST enzyme.

SUMMARY OF THE INVENTION

The present invention provides nucleic acid fragments isolated from maize encoding all or a substantial portion of a GST enzyme. The isolated nucleic acid fragment is selected from the group consisting of (a) an isolated nucleic acid fragment encoding all or a substantial portion of the amino acid sequence selected from the group consisting of SEQ ID NO:2, SEQ ID NO:4. SEQ ID NO:6, SEQ ID NO:8, SEQ ID NO:10, SEQ ID NO:12, SEQ ID NO:14 SEQ ID NO:16, SEQ ID NO:18, SEQ ID NO:20, SEQ ID NO:22, and SEQ ID NO:24, (b) an isolated nucleic acid fragment that is substantially similar to an isolated nucleic acid fragment encoding all or a substantial portion of the amino acid sequence sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, and SEQ ID NO:24; and (c) an isolated nucleic acid fragment that is complementary to (a) or (b). The nucleic acid fragments and corresponding polypeptides are contained in the accompanying Sequence Listing and described in the Brief Description of the Invention.

In another embodiment, the instant invention relates to chimeric genes encoding maize GST enzymes or to chimeric genes that comprise nucleic acid fragments as described above, the chimeric genes operably linked to suitable regulatory sequences, wherein expression of the chimeric genes results in altered levels of the encoded enzymes in transformed host cells.

The present invention further provides a transformed host cell comprising the above described chimeric gene. The transformed host cells can be of eukaryotic or prokaryotic origin. The invention also includes transformed plants that arise from transformed host cells of higher plants, and from seeds derived from such transformed plants, and subsequent progeny.

Additionally, the invention provides methods of altering the level of expression of a maize GST enzyme in a host cell comprising the steps of; (i) transforming a host cell with the above described chimeric gene and; (ii) growing the transformed host cell produced in step (i) under conditions that are suitable for expression of the chimeric gene wherein expression of the chimeric gene results in production of altered levels of a plant GST enzyme in the transformed host cell relative to expression levels of an untransformed host cell.

In an alternate embodiment, the present invention provides methods of obtaining a nucleic acid fragment encoding all or substantially all of the amino acid sequence encoding a maize GST enzyme comprising either hybridization or primer-directed amplification methods known in the art and using the above described nucleic acid fragment. A primer-amplification-based method uses SEQ ID NOS.: 1, 3, 5, 7, 9, 11, 13, 15, 17, 19, 21, or 23. The product of these methods is also part of the invention.

Another embodiment of the invention includes a method for identifying a compound that inhibits the activity of a maize GST enzyme encoded by the nucleic acid fragment and substantially similar and complementary nucleic acid fragments of SEQ ID NOS.:1–24. The method has the steps: (a) transforming a host cell with the above described chimeric gene; (b) growing the transformed host cell under conditions that are suitable for expression of the chimeric gene wherein expression of the chimeric gene results in production of the GST enzyme; (c) optionally purifying the GST enzyme expressed by the transformed host cell; (d) contacting the GST enzyme with a chemical compound of interest; and (e) identifying the chemical compound of interest that reduces the activity of the maize GST enzyme relative to the activity of the maize GST enzyme in the absence of the chemical compound of interest.

This method may further include conducting step (d) in the presence of at least one electrophilic substrate and at least one thiol donor. The isolated nucleic acid fragments of this method are chosen from the group represented by SEQ ID NOS.: 1, 3, 5, 7, 9, 11, 13, 15, 17, 19, 21, and 23, and the maize GST enzyme is selected from the group consisting of SEQ ID NOS.: 2, 4, 6, 8, 10, 12, 14, 16, 18, 20, 22, and 24.

The invention further provides a method for identifying a chemical compound that inhibits the activity of the maize GST enzyme as described herein, wherein the identification is based on a comparison of the phenotype of a plant transformed with the above described chimeric gene contacted with the inhibitor candidate with the phenotype of a transformed plant that is not contacted with the inhibitor candidate. The isolated nucleic acid fragment of this method is selected from the group consisting of SEQ ID NOS.: 1, 3, 5, 7, 9, 11, 13, 15, 17, 19, 21, and 23 and the maize GST enzyme is selected from the group consisting of SEQ ID NOS.: 2, 4, 6, 8, 10, 12, 14, 16, 18, 20, 22, and 24.

In another embodiment, the invention provides a method for identifying a substrate for the maize GST enzyme. The method comprises the steps of: (a) transforming a host cell with a chimeric gene comprising the nucleic acid fragment as described herein, the chimeric gene encoding a maize GST enzyme operably linked to at least one suitable regulatory sequence; (b) growing the transformed host cell of step (a) under conditions that are suitable for expression of the chimeric gene resulting in production of the GST enzyme; (c) optionally purifying the GST enzyme expressed by the transformed host cell; (d) contacting the GST enzyme with a substrate candidate; and (e) comparing the activity of maize GST enzyme with the activity of maize GST enzyme that has been contacted with the substrate candidate and selecting substrate candidates that increase the activity of the maize GST enzyme relative to the activity of maize GST enzyme in the absence of the substrate candidate. More preferably, step (d) of this method is carried out in the presence of at least one thiol donor. The isolated nucleic acid fragment of this method is selected from the group consisting of SEQ ID NOS.: 1, 3, 5, 7, 9, 11, 13, 15, 17, 19, 21, and 23, 25 and the maize GST enzyme is selected from the group consisting of SEQ ID NOS.: 2, 4, 6, 8, 10, 12, 14, 16, 18, 20, 22, and 24.

Alternatively, methods are provided for identifying a maize GST substrate candidate wherein the identification of the substrate candidate is based on a comparison of the phenotype of a host cell transformed with a chimeric gene expressing a maize GST enzyme and contacted with a substrate candidate with the phenotype of a similarly transformed host cell grown without contact with a substrate candidate.

The isolated nucleic acid fragment of this method is selected from the group consisting of SEQ ID NOS.: 1, 3, 5, 7, 9, 11, 13, 15, 17, 19, 21, and 23 and the maize GST enzyme is selected from the group consisting of SEQ ID NOS.: 2, 4, 6, 8, 10, 12, 14, 16, 18, 20, 22, and 24.

BRIEF DESCRIPTION OF SEQUENCE DESCRIPTIONS AND BIOLOGICAL DEPOSITS

The invention can be more fully understood from the following detailed description and the accompanying sequence descriptions and biological deposits which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence comprising the cDNA insert in clone bms1.pk0023.g8 encoding a maize GST.

SEQ ID NO:2 is the deduced amino acid sequence of the nucleotide sequence comprising the cDNA insert in clone bms1.pk0023.g8.

SEQ ID NO:3 is the nucleotide sequence comprising the cDNA insert in clone cs.pk0010.c5 encoding a maize GST.

SEQ ID NO:4 is the deduced amino acid sequence of the nucleotide sequence comprising the cDNA insert in clone cs.pk0010.c5.

SEQ ID NO:5 is the nucleotide sequence comprising the cDNA insert in clone ceb1.pk0017.a5 encoding a maize GST.

SEQ ID NO:6 is the deduced amino acid sequence of the nucleotide sequence comprising the cDNA insert in clone ceb1.pk0017.a5.

SEQ ID NO:7 is the nucleotide sequence comprising the cDNA insert in clone cc71se-a.pk0001.g2 encoding a maize class III GST.

SEQ ID NO:8 is the deduced amino acid sequence of the nucleotide sequence comprising the cDNA insert in clone cc71se-a.pk0001.g2.

SEQ ID NO:9 is the nucleotide sequence comprising the cDNA insert in clone cc71se-b.pk0014.b8 encoding a maize class III GST.

SEQ ID NO:10 is the deduced amino acid sequence of the nucleotide sequence comprising the cDNA insert in clone cc71se-b.pk0014.b8.

SEQ ID NO:11 is the nucleotide sequence comprising the cDNA insert in clone ceb5.pk0051.f8 encoding a maize class III GST.

SEQ ID NO:12 is the deduced amino acid sequence of the nucleotide sequence comprising the cDNA insert in clone ceb5.pk0051.f8.

SEQ ID NO:13 is the nucleotide sequence comprising the cDNA insert in clone cr1n.pk0003.b1 encoding a maize class III GST.

SEQ ID NO:14 is the deduced amino acid sequence of the nucleotide sequence comprising the cDNA insert in clone cr1n.pk0003.b1.

SEQ ID NO:15 is the nucleotide sequence comprising the cDNA insert in clone cr1n.pk0014.g8 encoding a maize class III GST.

SEQ ID NO:16 is the deduced amino acid sequence of the nucleotide sequence comprising the cDNA insert in clone cr1n.pk0014.g8.

SEQ ID NO:17 is the nucleotide sequence comprising the cDNA insert in clone m.15.5.d06.sk20 encoding a maize class II GST.

SEQ ID NO:18 is the deduced amino acid sequence of the nucleotide sequence comprising the cDNA insert in clone m.15.5.d06.sk20.

SEQ ID NO:19 is the nucleotide sequence comprising the cDNA insert in clone cr1n.pk0040.e12 encoding a maize class II GST.

SEQ ID NO:20 is the deduced amino acid sequence of the nucleotide sequence comprising the cDNA insert in clone cr1n.pk0040.e12.

SEQ ID NO:21 is the nucleotide sequence comprising the cDNA insert in clone ceb5.pk0049.a11 encoding a maize class III GST.

SEQ ID NO:22 is the deduced amino acid sequence of the nucleotide sequence comprising the cDNA insert in clone ceb5.pk0049.a11.

SEQ ID NO:23 is the nucleotide sequence comprising the cDNA insert in clone cs1.pk0059.e2 encoding a maize class III GST. SEQ ID NO:24 is the deduced amino acid sequence of the nucleotide sequence comprising the cDNA insert in clone cs1.pk0059.e2.

The transformed *E. coli* ceb5.pk0051.f8/pET30(LIC) BL21(DE3) containing the gene ceb5.pk0051.f8 in a pET30 (LIC) vector encoding a maize class III GST was deposited on Aug. 21, 1997 with the American Type Culture Collection (ATCC), 12301 Parklawn Drive, Rockville, Md. 20852, U.S.A., under the terms of the Budapest Treaty on the International Recognition of the Deposit of Microorganisms for the Purpose of Patent Procedure. The deposit is designated as ATCC 98511.

DETAILED DESCRIPTION OF THE INVENTION

The present invention provides novel GST nucleotide sequences and encoded proteins isolated from maize. GST enzymes are known to function in the process of detoxification of a variety of xenobiotic compounds in plants, most notably, herbicides. Nucleic acid fragments encoding at least a portion of several maize GST enzymes have been isolated and identified by comparison of random plant cDNA sequences to public databases containing nucleotide and protein sequences using the BLAST algorithms well known to those skilled in the art. The sequences of the present invention are useful in the construction of herbicide-tolerant transgenic plants, in the recombinant production of GST enzymes, in the development of screening assays to identify compounds inhibitory to the GST enzymes, and in screening assays to identify chemical substrates of the GSTs.

In the context of this disclosure, a number of terms shall be utilized.

As use herein "Glutathione S-Transferase" or "GST" refers to any plant derived glutathione S-transferase (GST) enzyme capable of catalyzing the conjugation of glutathione, homoglutathione and other glutathione-like analogs via a sulfhydryl group, to hydrophobic and electrophilic compounds. The term GST includes amino acid sequences longer or shorter than the length of natural GSTs, such as functional hybrid or partial fragments of GSTs, or their analogues. As used herein "GST" is not intended to be delimited on the basis of enzyme activity but may encompass amino acid sequences that possess no measurable enzyme activity but are substantially similar in to those sequences, known in the art to possess the above mentioned glutathione conjugating activity.

The term "class" or "GST class" refers to a grouping of the various GST enzymes according to amino acid identity. Currently, four classes have been identified and are referred to as "GST class I" "GST class II", "GST class III" and "GST class IV". The grouping of plant GSTs into three classes is described by Droog et al. (*Plant Physiology* 107:1139–1146 (1995)). All available amino acid sequences were aligned using the Wisconsin Genetics Computer Group package (Wisconsin Package Version 9.0, Genetics Computer Group (GCG), Madison, Wis.), and graphically represented on a phylogenetic tree. Three groups were identified: class one including the archetypical sequences from maize GST I (X06755) and GST III (X04375); class two including the archetypical sequence from *Dianthus caryophyllus* (M64628); and class three including the archetypical sequence soybean GH2/4 (M20363). Recently, Applicants have established a further subgroup of the plant GSTs known as class IV GSTs with its archetypical sequence being In2-1 (X58573).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.). with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the GST enzymes as set forth in SEQ ID Nos: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, and SEQ ID NO:24. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence: The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. ((1989) *Plant Cell* 1:671–680).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

The term "herbicide-tolerant plant" as used herein is defined as a plant that survives and preferably grows normally at a usually effective dose of a herbicide. Herbicide tolerance in plants according to the present invention refers to detoxification mechanisms in a plant, although the herbicide binding or target site is still sensitive.

"Thiol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheramones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

"Thiol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheramones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other GST enzymes, either as cDNAs or genomic DNAs, could be isolated directly by using all or a portion of the instant nucleic acid fragments as DNA hybridization probes to screen libraries from any desired plant using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed GST enzymes are present at higher or lower levels than normal or in cell types or developmental stages in which they are not normally found. This would have the effect of altering the level of GST enzyme available as well as the herbicide tolerant-phenotype of the plant.

Overexpression of the GST enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a GST coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence for GST, should be capable of promoting expression of the GST such that the transformed plant is tolerant to an herbicide due to the presence of, or increased levels of, GST enzymatic activity. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective* A. Cashmore, Plenum, New York (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.*, 618 (1–2) (1993) 133–145), Western analysis of protein expression, or phenotypic analysis.

For some applications it will be useful to direct the instant GST enzymes to different cellular compartments or to facilitate enzyme secretion from a recombinant host cell. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

It may also be desirable to reduce or eliminate expression of the genes encoding the instant GST enzymes in plants for some applications. In order to accomplish this, chimeric genes designed for co-suppression of the instant GST enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

Plants transformed with the present GST genes will have a variety of phenotypes corresponding to the various properties conveyed by the GST class of proteins. Glutathione conjugation catalyzed by GSTs is known to result in sequestration and detoxification of a number of herbicides and other xenobiotics (Marrs et al., *Annu. Rev. Plant Physiol. Plant Mol. Biol.* 47:127–58 (1996)) and thus will be expected to produce transgenic plants with this phenotype. Other GST proteins are known to be induced by various environmental stresses such as salt stress (Roxas, et al., *Stress tolerance in transgenic seedlings that overexpress glutathione S-transferase,* Annual Meeting of the American Society of Plant Physiologists, (August 1997), abstract 1574, Final Program, Plant Biology and Supplement to Plant Physiology, 301), exposure to ozone (Sharma et al., *Plant Physiology,* 105 (4) (1994)1089–1096), and exposure to industrial pollutants such as sulfur dioxide (Navari-Izo et al., *Plant Science* 96 (1–2) (1994) 31–40). It is contemplated that transgenic plants, tolerant to a wide variety of stresses, may be produced by the present method by expressing foreign GST genes in suitable plant hosts.

The instant GST enzymes produced in heterologous host cells, particularly in the cells of microbial hosts, can be used to prepare antibodies to the enzymes by methods well known to those skilled in the art. The antibodies are useful for detecting the enzymes in situ in cells or in vitro in cell extracts. Preferred heterologous host cells for production of the instant GST enzymes are microbial hosts. Microbial expression systems and expression vectors containing regulatory sequences that direct high level expression of foreign proteins are well known to those skilled in the art. Any of these could be used to construct chimeric genes for production of the instant GST enzymes. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the GST enzymes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary, however, it is most preferred if included.

An example of a vector for high level expression of the instant GST enzymes in a bacterial host is provided (Example 5).

Additionally, the instant maize GST enzymes can be used as a targets to facilitate design and/or identification of inhibitors of the enzymes that may be useful as herbicides or herbicide synergists. This is desirable because the enzymes described herein catalyze the sulfhydryl conjugation of glutathione to compounds toxic to the plant. Conjugation can result in detoxification of these compounds. It is likely that inhibition of the detoxification process will result in inhibition of plant growth or plant death. Thus, the instant maize GST enzymes could be appropriate for new herbicide or herbicide synergist discovery and design.

All or a portion of the nucleic acid fragments of the instant invention may also be used as probes for genetically and physically mapping the genes that they are a part of, and as markers for traits linked to expression of the instant enzymes. Such information may be useful in plant breeding in order to develop lines with desired phenotypes or in the identification of mutants.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., (1980) *Am. J. Hum. Genet.* 32:314–331).

The production and use of plant gene-derived probes for use in genetic mapping are described by Bernatzky, R. and Tanksley, S. D. (*Plant Mol. Biol. Reporter* 4(1):37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS); allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods. Such information may be useful in plant breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1

Composition of cDNA Libraries, Isolation and Sequencing of cDNA Clones cDNA libraries representing mRNAs from various maize tissues were prepared. The characteristics of the libraries are described in Table 1.

TABLE 1 cDNA Libraries From Corn Tissues

| Library | GST Class | Clone | Tissue |
| --- | --- | --- | --- |
| bms1 | I | bms1.pk0023.g8 | Maize BMS cell culture 1 day after subculture |
| cs1 | I | cs1.pk0010.c5 | Maize leaf, sheath 5 wk plant Stratogene #837201 |
| ceb1 | I | ceb1.pk0017.a5 | Maize embryo |
| cc71se | III | cc71se-a.pk0001.g2 | Maize class II callus tissue, somatic embryo formed, highly transformable |
| cc71se | III | cc71se-b.pk0014.b8 | Maize class II callus tissue, somatic embryo formed, highly transformable |
| ceb5 | III | ceb5.pk0051.f8 | Amplified maize embryo 30 day |
| cr1n | III | cr1n.pk0003.b1 | Maize root from 7 day seedlings grown in light normalized |
| cr1n | III | cr1n.pk0014.g8 | Maize root from 7 day seedlings grown in light normalized |
| m | II | m.15.5.d06.sk20 | Maize 15 day embryo library |
| cr1n | II | cr1n.pk0040.e12 | Maize root from 7 day seedlings grown in light normalized |
| ceb5 | III | ceb5.pk0049.a11 | Amplified maize embryo 30 day |

TABLE 1-continued cDNA Libraries From Corn Tissues

| Library | GST Class | Clone | Tissue |
|---|---|---|---|
| cs1 | III | cs1.pk0059.e2 | Maize leaf, sheath 5 wk plant Stratogene #837201 | cDNA libraries were prepared in Uni-ZAP™ XR vectors according to the manufacturer's protocol (Stratagene Cloning Systems, La Jolla, Calif.). The Uni-ZAP™ XR libraries were converted into plasmid libraries according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification and Characterization of cDNA Clones cDNAs encoding maize GST enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

All comparisons were done using the BLASTNnr algorithm with the exception of cr1n.pk0040.e12 where BLASTXnr was used. The results of the BLAST comparison is given in Table 2 and summarizes the clones and the sequences to which they have the most similarity. Each cDNA identified encodes at least a portion of either a GST class I, II, or III. All isolated clones contain a full length open reading frame (ORF) with the exception of cc71se-a.pk0001.g2 which is only a partial clone. Example 5 describes the sequencing strategy for the above described clones.

TABLE 2

BLAST Results For Clones

| Clone | GST Class | Similarity Identified | SEQ ID NO Base | Peptide | Blast Algorithm | pLog Score |
|---|---|---|---|---|---|---|
| bms1.pk0023.g8 | I | X79515\|ZMGST27 Z.mays GST-27 mRNA for glutathione-S-transferase | 1 | 2 | Nnr | 122.086 |
| cs1.pk0010.c5 | I | D17673\|ATHERD13 Arabidopsis thaliana mRNA for glutathione S-transferase | 3 | 4 | Nnr | 8.16 |
| ceb1.pk0017.a5 | I | X78203\|HMGST H.muticus mRNA for glutathione S-transferase | 5 | 6 | Nnr | 21.51 |
| cc71se-a.pk0001.g2 | III | (AF004358) glutathione S-transferase TSI-1 (Aegilops squarrosa) | 7 | 8 | Nnr | 16.48 |
| cc71se-b.pk0014.b8 | III | D10861\|RICORFC Rice mRNA for a protein related to chilling tolerance. | 9 | 10 | Nnr | 14.96 |
| ceb5.pk0051.f8 | III | D10861\|RICORFC Rice mRNA for a protein related to chilling tolerance. | 11 | 12 | Nnr | 40.44 |
| cr1n.pk0003.b1 | III | U80615\|EGU80615 Eucalyptus globulus auxin-induced protein (EgPar) mRNA, complete cds | 13 | 14 | Nnr | 24.70 |
| cr1n.pk0014.g8 | III | M16901\|MZEGSTIB Maize glutathione S-transferase (GST-I) mRNA, complete cds | 15 | 16 | Nnr | 5.85 |
| m.15.5.d06.sk20 | II | \|M97702\|DROGLUSTD Drosophila melanogaster glutathione S-transferase gene. | 17 | 18 | Nnr | 3.63 |
| cr1n.pk0040.e12 | II | 167970 (L05915) (GST1) gene product (Dianthus caryophyllus) | 19 | 20 | Xnr | 42.03 |

TABLE 2-continued

BLAST Results For Clones

|  |  |  | SEQ ID NO |  |  |  |
|---|---|---|---|---|---|---|
| Clone | GST Class | Similarity Identified | Base | Peptide | Blast Algorithm | pLog Score |
| ceb5.pk0049.a11 | III | \|Y12862\|ZYMY12862 Zea Maize mRNA for glutathione S-transferase | 21 | 22 | Nnr | 0.0 |
| cs1.pk0059.e2 | III | D10861\|RICORFC Rice mRNA for a protein related to chilling tolerance. | 24 | 25 | Nnr | 41.03 |

Example 3

Expression of Chimeric Genes Encoding Maize GST Enzymes in Maize Cells (Monocotyledon)

A chimeric gene comprising a cDNA encoding a maize GST enzyme in sense orientation can be constructed by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 µL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML 103. Plasmid pML 103 has been deposited under the terms of the Budapest Treaty at ATCC (American Type Culture Collection, 12301 Parklawn Drive, Rockville, Md. 20852), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp 7113 Benhart Dr, Raleigh, N.C.). Vector and insert DNA can be ligated at 15° C. overnight, essentially as described (Maniatis). The ligated DNA may then be used to transform E. coli XL1-Blue (Epicurian Coli XL-1; Stratagene). Bacterial transformants can be screened by restriction enzyme digestion of plasmid DNA and limited nucleotide sequence analysis using the dideoxy chain termination method DNA Sequencing Kit; U.S. Biochemical). The resulting plasmid construct would comprise a chimeric gene encoding, in the 5' to 3' direction, the maize 27 kD zein promoter, a cDNA fragment encoding a plant GST enzyme, and the 10 kD zein 3' region. The chimeric gene described above can then be introduced into corn cells by the following procedure. Immature corn embryos can be dissected from developing caryopses derived from crosses of the inbred corn lines H99 and LH132 (Indiana Agric. Exp. Station, Ind., USA). The embryos are isolated 10 to 11 days after pollination when they are 1.0 to 1.5 mm long. The embryos are then placed with the axis-side facing down and in contact with agarose-solidified N6 medium (Chu et al., (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3M region of the nopaline synthase gene from the T-DNA of the Ti plasmid of Agrobacterium tumefaciens. The particle bombardment method (Klein et al., (1987) Nature 327:70–73) may be used to transfer genes to the callus culture cells. According to this method, gold particles ((1 µm in diameter) are coated with DNA using the following technique. Ten ug of plasmid DNAs are added to 50 uL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 uL of ethanol. An aliquot (5 µL) of the DNA-coated gold particles can be placed in the center of a flying disc (Bio-Rad Labs, 861 Ridgeview Dr, Medina, Ohio). The particles are then accelerated into the corn tissue with a PDS- 1000/He (Bio-Rad Labs, 861 Ridgeview Dr, Medina, Ohio), using a helium pressure of 1000 psi, a gap distance of 0.5 cm and a flying distance of 1.0 cm. For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi. Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) Bio/Technology 8:833–839).

Example 4

Expression of Chimeric Genes in Tobacco Cells (Dicotyledon)

Cloning sites (XbaI or SmaI) can be incorporated into the oligonucleotides to provide proper orientation of the DNA fragment when inserted into the digested vector pBI121 (Clonetech Inc., 6500 Donlon Rd, Somis, Calif.) or other appropriate transformation vector. Amplification could be performed as described above and the amplified DNA would then be digested with restriction enzymes XbaI and SmaI and fractionated on a 0.7% low melting point agarose gel in 40 mM Tris-acetate, pH 8.5, 1 mM EDTA. The appropriate band can be excised from the gel, melted at 68° C. and combined with a 13 kb XbaI-SmaI fragment of the plasmid pBI121 and handled as in Example 3. The resulting plasmid construct would comprise a chimeric gene encoding, in the 5' to 3' direction, right border region, the nos promoter linked to the NPT II gene and a nos terminator region followed by a cauliflower mosaic virus 35S promoter linked to a cDNA fragment encoding a plant GST enzyme and the nos terminator 3' region flanked by the left border region. The resulting plasmid could be mobilized into the Agrobacterium strain LBA4404/pAL4404 (Hoekema et al. *Nature* 303:179–180, (1983) using tri-parental matings (Ruvkin and Ausubel, *Nature* 289:85–88, (1981)). The resulting Agrobacterium strains could be then cocultivated with protoplasts (van den Elzen et al. *Plant Mol. Biol,* 5:149–154 (1985)) or leaf disks (Horsch et al. *Science* 227:1229–1231, (1985)) of *Nicotiana tabacum* cv Wisconsin 38 and kanamycin-resistant transformants would be selected. Kanamycin-resistant transformed tobacco plants would be regenerated.

Example 5

Expression of Chimeric Genes in Microbial Cells and Purification of Gene Product Example 5 illustrates the expression of isolated fill length genes encoding either class I, II or III GST proteins in *E coli*.

All clones listed in Table 2 were selected on the basis of homology to known GSTs using the BLAST algorithm as described in Example 2. Plasmid DNA was purified using QIAFilter cartridges (Qiagen. Inc., 9600 De Soto Ave, Chatsworth, Calif.) according to the manufacturer's instructions. Sequence was generated on an ABI Automatic sequencer using dye terminator technology (U.S. Pat. No. 5,366,860; EP 272007) using a combination of vector and insert-specific primers. Sequence editing was performed in either DNAStar (DNA, Star Inc.) or the Wisconsin GCG program (Wisconsin Package Version 9.0, Genetics Computer Group (GCG), Madison, Wis.). All sequences represent coverage at least two times in both directions.

cDNA from the clones bms1.pk0023.g8, cs1.pk0010.c5, ceb1.pk0017.a5, m.15.5.d06.sk20, ceb5.pk0049.a11, ceb5.pk0051.f8, and cs1.pk0059.e2, encoding the instant maize GST enzymes were inserted into the ligation independent cloning (LIC) pET30 vector (Novagen, Inc., 597 Science Dr, Madison, Wis.) under the control of the T7 promoter, according to the manufacturer's instructions (see Novagen publications "LIC Vector Kits", publication number TB163 and U.S. Pat. No. 4,952,496). The vector was then used to transform BL21 (DE3) competent *E. coli* hosts. Primers with a specific 3' extension designed for ligation independent cloning were designed to amplify the GST gene (Maniatis). Amplification products were gel-purified and annealed into the LIC vector after treatment with T4 DNA polymerase (Novagen). Insert-containing vectors were then used to transform NovaBlue competent *E. coli* cells and transformants were screened for the presence of viable inserts. Clones in the correct orientation with respect to the T7 promoter were transformed into BL21 (DE3) competent cells (Novagen) and selected on LB agar plates containing 50 μg/mL kanamycin. Colonies arising from this transformation were grown overnight at 37° C. in Lauria Broth to OD 600=0.6 and induced with 1 mM IPTG and allowed to grow for an additional two hours. The culture was harvested, resuspended in binding buffer, lysed with a French press and cleared by centrifugation.

Expressed protein was purified using the HIS binding kit (Novagen) according to the manufacturer's instructions. Purified protein was examined on 15–20% SDS Phast Gels (Bio-Rad Laboratories, 861 Ridgeview Dr, Medina, Ohio) and quantitated spectrophotometrically using BSA as a standard. Protein data is tabulated below in Table 3.

TABLE 3

| Protein Expression Data | |
| --- | --- |
| CLONE | OD.280 |
| bms1.pk0023.g8 | 0.57 |
| cs1.pk0010.c5 | 0.53 |
| ceb1.pk0017.a5 | 0.50 |
| m.15.5.d06.sk20 | 0.39 |
| ceb5.pk0049.a11 | 2.06 |
| ceb5.pk0051.f8 | 1.30 |
| cs1.pk0059.e2 | 1.45 |

Example 6

Screening of Expressed GST Enzymes for Substrate Metabolism

The GST enzymes, expressed and purified as described in Example 5 were screened for their ability to metabolize a variety of substrates. Substrates tested included the three herbicide electrophilic substrates chlorimuron ethyl, alachlor, and Atrazine, and four model electrophilic substrates, 1-chloro-2,4-dinitrobenzene (CDNB), ethacrynic acid, t-stilbene oxide, and 1,2-epoxy-3-(p-nitrophenoxy) propane. The enzymes were purified as described in Example 5 and used in the following assay.

For each enzyme, the conjugation reaction with each electrophilic substrate was performed by incubating 0.3 to 30 μg enzyme in 0.1 M MOPS (pH 7.0) containing 0.4 mM of the electrophilic substrate. The reaction was inititated by the addition of glutathione to a final concentration of 4 mM. After 5 to 30 min, the reaction was terminated by the addition of 45 μL acetonitrile, microfuged for 10 min to remove precipitated protein, and then the supernatent was removed and added to 65 µl of water. This sample was chromatographed on Zorbax C8 reverse phase HPLC column (3 µm particle size, 6.2 mm×8 cm) using a combination of linear gradients (flow=1.5 mL/min) of 1% $H_3PO_4$ in water (solvent A) and 1% $H_3PO_4$ in acetonitrile. The gradient started with 5% solvent B, progressing from 5% to 75% solvent B between 1 and 10 min, and from 75% to 95% solvent B between 10 and 12 min. Control reactions without enzyme were performed to correct for uncatalyzed reaction. Quantitation of metabolites were based on an assumption that the extinction coefficient of the conjugate was identical to that of the electrophilic substrate.

Table 4 shows the activity of each enzyme measured in nmol·min$^{-1}$·mg$^{-1}$ with the seven different substrates. Activities are related to the activities of the known and previously isolated and purified GST enzymes, BZ-II (Marrs et al., *Nature* 375:397–400 (1995)), pIN2-1 (Hershey et al., *Plant Molecular Biology* 17:679–690, (1991)), GST-I, GST-III, and GST-IV, collectively described in Shah et al., *Plant Mol Biol* 6, 203–211 (1986); Jepson et al., *Plant Mol Biol* 26:1855–1866, (1994); Moore et al., *Nucleic Acids Res* 14:7227–7235 (1986); and Holt et al., *Planta* 196:295–302, (1995).

TABLE 4

| GST Name | GST Class | Chlor-Imuron-Ethyl | Alachlor | Atrazine | CDNB | Ethacrynic Acid | t-Stilbene Oxide | 1,2-epoxy-3-(p-nitrophenoxy)propane |
|---|---|---|---|---|---|---|---|---|
| cs1.pk0059.e2 | III | 0.1 | 8 | 0.02 | 1348 | 20 | 1.25 | 43 |
| ceb5.pk0049.a11 | III | 0.4 | 18 | 0.01 | 3939 | 102 | 0.01 | 30 |
| ceb5.pk0051.f8 | III | 1.9 | 27 | 0.08 | 2136 | 117 | 0.02 | 14 |
| BZ-II | III | 0.2 | 0 | 0.00 | 15 | 23 | 0.05 | 0 |
| ceb1.pk0017.a5 | I | 0.1 | 0 | 0.00 | 15 | 5 | 0.00 | 0 |
| cs1.pk0010.c5 | I | 0.1 | 0 | 0.00 | 30 | 9 | 0.00 | 0 |
| bms1.pk0023.g8 | I | 0.2 | 0 | 0.00 | 15 | 13 | 0.00 | 0 |
| GST-IV | I | 0.3 | 1 | 0.00 | 15 | 13 | 0.00 | 0 |
| GST-I | I | 0.4 | 77 | 0.60 | 46485 | 32 | 0.98 | 92 |
| GST-III | I | 0.3 | 3 | 0.05 | 1803 | 1 | 0.31 | 28 |
| m.15.5.d06.sk20 | II | 0.1 | 0 | 0.00 | 45 | 17 | 0.00 | 1 |
| pIN2-1 | IV | 0 | 0 | — | 15 | — | — | — |

What is claimed is:

1. An isolated nucleic acid fragment encoding a Glutathione S-Transferase enzyme selected from the group consisting of:
   (a) an isolated nucleic acid molecule encoding the amino acid sequence set forth in SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, and SEQ ID NO:24 or an enzymatically active fragment thereof;
   (b) an isolated nucleic acid molecule that hybridizes with SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21, and SEQ ID NO:23 under the following hybridization conditions: 0.1X SSC, 0.1% SDS at 65 degrees C; and
   (c) an isolated nucleic acid molecule that is completely complementary to (a) or (b).

2. The isolated nucleic acid fragment of claim 1 selected from the group consisting of SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, and SEQ ID NO:23.

3. A chimeric gene comprising the isolated nucleic acid fragment of claim 1 operably linked to suitable regulatory sequences.

4. A transformed host cell comprising a host cell and the chimeric gene of claim 3.

5. The transformed host cell of claim 4 wherein the host cell is a plant cell.

6. The chimeric host cell of claim 4 wherein the host cell is E. coli.

7. A method of altering the level of expression of a Glutathione S-Transferase enzyme in a host cell comprising:
   (a) transforming a host cell with the chimeric gene of claim 5 and;
   (b) growing the transformed host cell produced in step (a) under conditions that are suitable for expression of the chimeric gene resulting in production of altered levels of a Glutathione S-Transferase enzyme in the transformed host cell relative to expression levels of an untransformed host cell.

8. A method of obtaining a nucleic acid fragment encoding all or a substantial portion of the amino acid sequence encoding a Glutathione S-Transferase enzyme comprising:
   (a) probing a cDNA or genomic library with a nucleic acid fragment that hybridizes with an isolated nucleic acid sequence selected from the group consisting of SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21, and SEQ ID NO:23;
   (b) identifying a DNA clone that hybridizes with the nucleic acid fragment of step (a); and
   (c) sequencing the cDNA or genomic fragment that comprises the clone identified in step (b),
   wherein the sequenced cNDA or genomic fragment encodes all or substantially all of the amino acid sequence encoding a Glutathione S-Transferase enzyme.

9. A method of obtaining a nucleic acid fragment encoding all or a substantial portion of the amino acid sequence encoding a Glutathione S-Transferase enzyme comprising:
   (a) synthesizing an oligonucleotide primer corresponding to a portion of the sequence selected from the group consisting of SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21, and SEQ ID NO:23;
   (b) amplifying a cDNA insert present in a cloning vector using the oligonucleotide primer of step (a) and a primer representing sequences of the cloning vector,
   wherein the amplified cDNA insert encodes a portion of an amino acid sequence encoding a Glutathione S-Transferase enzyme.

* * * * *